United States Patent
Ambrus et al.

(10) Patent No.: US 6,528,057 B1
(45) Date of Patent: Mar. 4, 2003

(54) METHOD FOR REMOVAL OF HIV AND OTHER VIRUSES FROM BLOOD

(76) Inventors: Julian L. Ambrus, 541 W. Ferry St., Buffalo, NY (US) 14222-1509; David O. Scamurra, 66 Four Seasons West 14226, Eggertsville, NY (US) 14226

(*) Notice: Subject to any disclaimer, the term of this patent is extended or adjusted under 35 U.S.C. 154(b) by 0 days.

(21) Appl. No.: 09/385,166

(22) Filed: Aug. 30, 1999

Related U.S. Application Data

(60) Provisional application No. 60/098,477, filed on Aug. 31, 1998.

(51) Int. Cl.$^7$ ............................................. A61K 39/00
(52) U.S. Cl. .................. 424/140.1; 210/645; 210/646; 435/4; 435/6; 435/7.1; 436/501; 530/388.1; 530/389.1; 530/389.4; 604/4.01; 604/5.01; 604/5.02
(58) Field of Search ................. 210/645, 646, 210/656; 530/388.1, 388.3, 389.1, 389.4; 536/23.72, 24.3; 604/4.01, 5.01, 5.02; 935/2; 435/4, 6, 7.1; 436/501; 924/140.1

(56) References Cited

U.S. PATENT DOCUMENTS

| | | | |
|---|---|---|---|
| 4,612,122 A | | 9/1986 | Ambrus et al. |
| 4,668,399 A | * | 5/1987 | Duggins ..................... 210/637 |
| 4,787,974 A | | 11/1988 | Ambrus et al. |
| 5,041,079 A | * | 8/1991 | Takashima et al. ............. 604/5 |
| 5,667,684 A | * | 9/1997 | Motomura et al. ......... 210/506 |
| 6,174,299 B1 | * | 1/2001 | Pollard et al. .................. 604/5 |

OTHER PUBLICATIONS

Zimmerman, et al. Generation of a Human Monoclonal Antibody to Hepatitis C virus, JRA1 by Activation of Peripheral Blood Lymphocytes and Hypo–Osmolar Electrofusion. Human Antibodies and Hybridomas. 1995, vol. 6, No. 2, pp. 77–80, see Abstract.

Batinic, et al, The V3 Region of the Envelope Glycoprotein of Human Immunodeficiency Virus Type 1 Binds Sulfated Polysaccharides and CD4–Derived Synthetic Peptides. Journal of Biological Chemistry. Apr. 5, 1992, vol. 267, No. 10, pp. 6664–6671, see Abstract.

Sherman, et al, Quantitative Evaluation of Hepatitis C Virus RNA in Patients with Concurrent Human Immunodeficiency Virus Infections. Journal of Clinical Microbiology. Oct. 1993. vol. 31, No. 10, pp. 2679–2682, see Abstract.

Chen, et al, Quantitative Detection of Hepatitis B Virus DNA in Human Sera by Branched–DNA Signal Amplification. Journal of Virological Methods. 1995, vol. 53, pp. 131–137, see entire document.

Deeks, et al, Variance of Plasma Human Immunodeficiency Virus Type 1 RNA Levels Measured by Branched DNA Within and Between Days. The Journal of Infectious Diseases. Aug. 1997, vol. 176, pp. 514–517, see entire document.

Urdea, et al, Direct and Quantitative Detection of HIV–1 RNA in Human Plasma with a Branched DNA Signal Amplification Assay. AIDS. 1993, vol. 7, Suppl. 2, pp. S11–S14, see entire document.

\* cited by examiner

*Primary Examiner*—James Housel
*Assistant Examiner*—Ulrike Winkler
(74) *Attorney, Agent, or Firm*—Hodgson Russ LLP

(57) ABSTRACT

This invention discloses a method for reducing the viral load by removal of viruses or fragments or components thereof from the blood by extracorporeally circulating blood through hollow fibers which have in the porous exterior surface, immobilized affinity molecules having specificity for viral components. Passage of the fluid through the hollow fibers causes the viral particles to bind to the affinity molecules thereby reducing the viral load in the effluent.

21 Claims, 4 Drawing Sheets

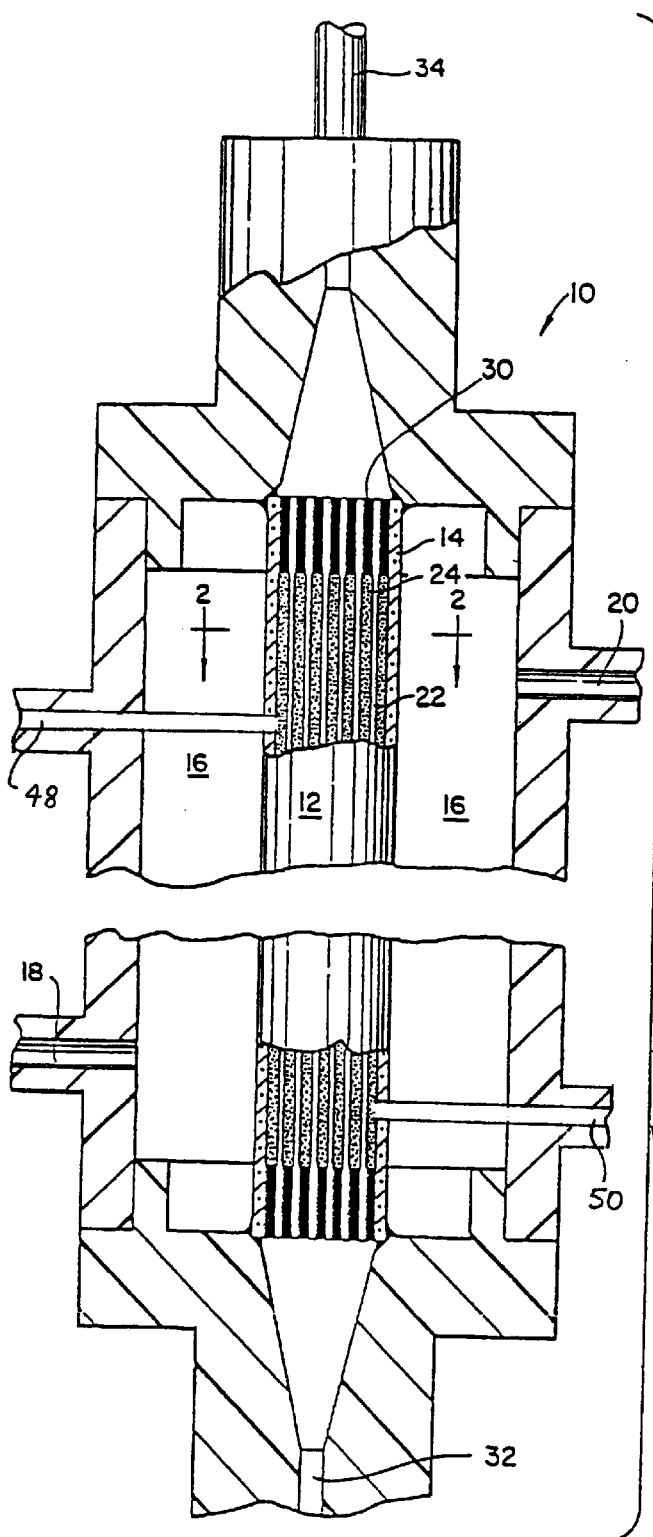
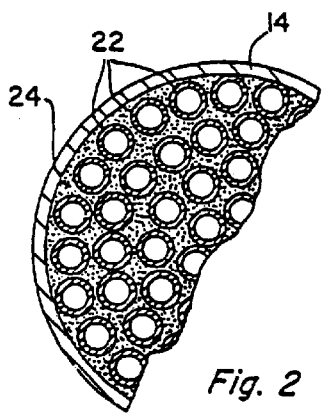
Fig. 1
Fig. 2
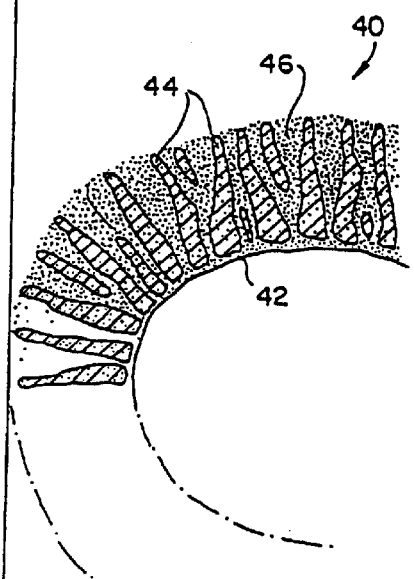
Fig. 3

SEQUENCE LISTING

```
<160> NUMBER OF SEQ ID NOS:  2

<210> SEQ ID NO 1
<211> LENGTH: 30
<212> TYPE: DNA
<213> ORGANISM: artificial sequence
<220> FEATURE:
<223> OTHER INFORMATION: completely synthesized; complementary to
      a conserved region in the 5' LTR of HIV-1

<400> SEQUENCE: 1
tccggtatag tggatcttga aatttacgta                                    30

<210> SEQ ID NO 2
<211> LENGTH: 29
```

-continued

```
<212> TYPE: DNA
<213> ORGANISM: artificial sequence
<220> FEATURE:
<223> OTHER INFORMATION: completely synthesized; complementary to
      5'NTR sequence of HCV

<400> SEQUENCE: 2
tctgacgatc ggctcatcca acccagcgc                                            29
```

METHOD FOR REMOVAL OF HIV AND OTHER VIRUSES FROM BLOOD

This application claims the priority of provisional application serial No. 60/098,477, filed on Aug. 31, 1998, the disclosure of which is incorporated herein by reference.

BACKGROUND OF THE INVENTION

1. Field of the Invention

This invention relates to the field of therapeutic methodologies for treating viral infections. More particularly, this invention provides a method for reducing the viral load by extracorporeal treatment of a patient's blood with immobilized molecules having specific affinity for viral components.

2. Description of Related Art

Human immunodeficiency virus (HIV) is the etiological agent of acquired immunodeficiency syndrome (AIDS) and infects selected cells of the immune system thereby compromising the infected individual's immune response. It is estimated that there are over 1 million HIV infected individuals in the United States and over 13 million world-wide. The clinical course of HIV infection typically consists of a prolonged asymptomatic state, followed by a depletion of T4 lymphocytes making the individual susceptible to opportunistic infections and neoplasms.

Currently there is no cure available for HIV infection. Mononucleoside drugs like AZT, dI, ddC and d4T, which inhibit the reverse transcriptase, have been approved for the treatment of HIV. Further, proteases inhibitors are also being now used. However, the emergence of drug resistant mutants limit the usefulness of these drugs.

The development of an effective vaccine against HIV infections has been hampered, in part, due to the rapid mutation of the HIV genome, and due to inaccessibility of immunogenic epitopes of viral proteins. The entire HIV genome has now been sequenced (Ratner et al., 1987, *AIDS Res. Hum. Retroviruses*, 3(1):57–69, incorporated herein by reference). The HIV genome encodes three major structural genes, gag, pol and env, which are flanked at either end by long terminal repeat (LTR) sequences. The HIV genes encode 3 viral enzymes, reverse transcriptase (p51+p66+RNase H), integrase (p32), and protease (p12), encased in a cylindrical protein core, composed predominantly of p24. Matrix protein (p17) and a lipid membrane, which contains two major envelope glycoproteins, gp41 and gp120, surround the protein core. The virion has a diameter of 110 nm (Gallo, 1995, Nat. Med., 1:753–759).

In order for HIV-1 to infect a cell, viral gp120 must bind to CD4 as well as to a surface chemokine receptor, generally CCR5(R5) or CxCR4(X4). Once endocytosed, the virion is uncoated. The viral RNA is reverse transcribed into double-stranded DNA, enters the cell nucleus and integrates into the host genome. Transcription of the integrated viral DNA results in the production of viral RNA, as well as various mRNA which are translated into viral proteins, some of which require further proteolytic processing. Mature virions are assembled and released from the cell by budding. (Fauci et al., 1996, Ann. Int. Med., 124:654–63). A dying cell may also release all its contents including intact virions, and fragments thereof into the blood. Thus, circulating blood of HIV-infected individuals contains both intact virions, fragments thereof and free RNA.

Isolates of HIV-1 from various donors show variability in surface glycoproteins. The variability in gp120 is more than the variability in gp41. Five variable regions are interspersed with conserved sequences within gp120. The majority of neutralizing antibodies to HIV-1 is directed towards the V3 loop of gp120, although some neutralizing antibodies also recognize the V2 and C4 domains, as well as epitopes in gp41. Within the V3 loop of gp120, the most highly conserved subdomain is glycine317-proline318-glycine319-arginine320-alanine321-phenylalanine322. Viruses with mutations involving glycine317-proline318-alanine319 are not infectious. Envelope sequences divides, HIV-1 into M and O groups. Within the M subgroups A–H are recognized, with subgroup B being prevalent in the United States.

HIV-1 replication occurs predominantly in CD4+ lymphocytes, the majority of which are located in lymphoid organs, such as peripheral lymph nodes and spleen. HIV-1 can also be found in macrophages and macrophage-like cells, such as microglia in the central nervous system (Cohen et al., 1997, *Immunol Rev.* 159:31–48). Plasma HIV-1 levels and presence of HIV-1 infected lymphocytes in peripheral blood strongly correlate with the clinical status of HIV-1 infected patients (Ferre et al., 1995, *J Acquir. Immnune Defic. Syndr. Hum. Retrovirol* 10:S51–6; Obrien et al., 1996, *N Engl J Med.*, 334:426–431). Half-life of circulating virions is 6 hours, while the half-life of HIV-1 infected cells in peripheral blood is 1.6 days. Greater than $10^{10}$ virions may be released into the circulation each day (Ho et al., 1995, *Nature* 373:123–126; Wei et al., 1995, *Nature* 373:117–122.). The ability of the host immune system to keep HIV infection in check, and limit clinical symptoms, is directly proportional to the viral burden. Anti-retroviral therapies, nucleoside analogues, non-nucleoside reverse transcriptase inhibitors, and protease inhibitors, aim to reduce the viral burden so that the immune system can control or clear residual infection (Fauci et al., 1998, *Harrison's Principles of Internal Medicine*, p. 1791–1856).

No previous technologies have been developed which directly absorb HIV from the blood using in vivo dialysis or immunoabsorption. Extracorporeal perfusion of plasma over protein A, plasmapheresis and lymphapheresis have all been used as immunomodulatory treatments for HIV infection, and the thrombocytopenia resulting from it (Kiprov, 1990, *Curr. Stud. Hematol. Blood Transfus.*, 57:184–97; Snyder et al., 1989, *Artif Organs* 13:71–7; Mittelman, 1989, *Semin Hematol* 26:15–8; Snyder et al., 1991, *AIDS* 5:1257–60.). These therapies are all proposed to work by removing immune complexes and other humoral mediators which are generated during HIV infection. They do not directly remove HIV virus. Extracorporeal photopheresis has been tested in preliminary trials as a mechanism to limit viral replication (Bisaccia et al., 1990, *Intern Med* 113:270–275; Bisaccia et al., 1993, *J. Acquir Immune. Defic. Syndr.* 6:386–92). It does not absorb virus from the blood. It has been reported that rabbit antisera raised against HIV proteins, when coupled to Sepharose 4B or Silica, could be used for extracorporeal removal of HIV proteins from the blood of rabbits which had been injected with recombinant HIV proteins (Lopukhin et al., 1991, Vestn Akad Med Nauk SSSR 11:60–3). This strategy was inefficient, and apparently not pursued. It required extracorporeal absorption of blood, and did not provide for a mechanism to remove free HIV viral particles from the blood (Lopukhin et al., 1991, supra).

Thus, there is an ongoing need for novel therapeutic approaches to the treatment of HIV and other viral infections. In particular, there is a need for the development of novel approaches to reduce the viral load so as to increase the effectiveness of other treatments and/or the immune response.

SUMMARY OF THE INVENTION

The present invention provides a method for reducing the viral load of patients. The method of the present invention involves removal of intact virions, fragments or components thereof including free viral nucleic acid from the blood by extracorporeally circulating blood through hollow fibers which have in the porous exterior surface, affinity molecules having specificity for viral components. Passage of the blood through the hollow fibers causes the virions and components thereof to bind to the affinity molecules thereby reducing the viral load in the effluent.

In one embodiment, this invention uses DNA sequences which have been shown to hybridize to many isolated subtypes of HIV-1 in vitro (Wilber, 1997, supra), and antibodies which have been shown to bind to intact virions of many HIV-1 subtypes in vitro (VanCott et al., 1994, Immunol. 153:449–59).

The method of the present invention reduces the number of virions in the blood, and thus contributes significantly to the reduction of viral load. It will be apparent to those skilled in the art that the device can be modified to assist in the clearance of other viral infections, frequently occurring simultaneously with HIV-1, such as cytomegalovirus (CMV), hepatitis B virus (HBV), and hepatitis C virus (HCV) (Fauci et al., 1998, supra).

Thus, an object of the invention is to provide a method for reducing the viral load in the blood of an individual infected with the virus.

Another object of the present invention is to provide a method for reducing the viral load in the blood by extracorporeal circulation of blood through hollow fibers containing immobilized molecules having specific affinity for viral components.

Another object of the present invention is to provide an apparatus comprising hollow fibers, wherein the exterior surface of the fibers is in close proximity with molecules having specific affinity for target molecules in the virus.

BRIEF DESCRIPTION OF THE DRAWINGS

FIG. 1 is a schematic illustration of a longitudinal cross section of an affinity cartridge.

FIG. 2 is a schematic illustration of a horizontal cross section at plane 2 in FIG. 1.

FIG. 3 is an illustration of a channel from FIG. 2.

DETAILED DESCRIPTION OF THE INVENTION

Figure 4:
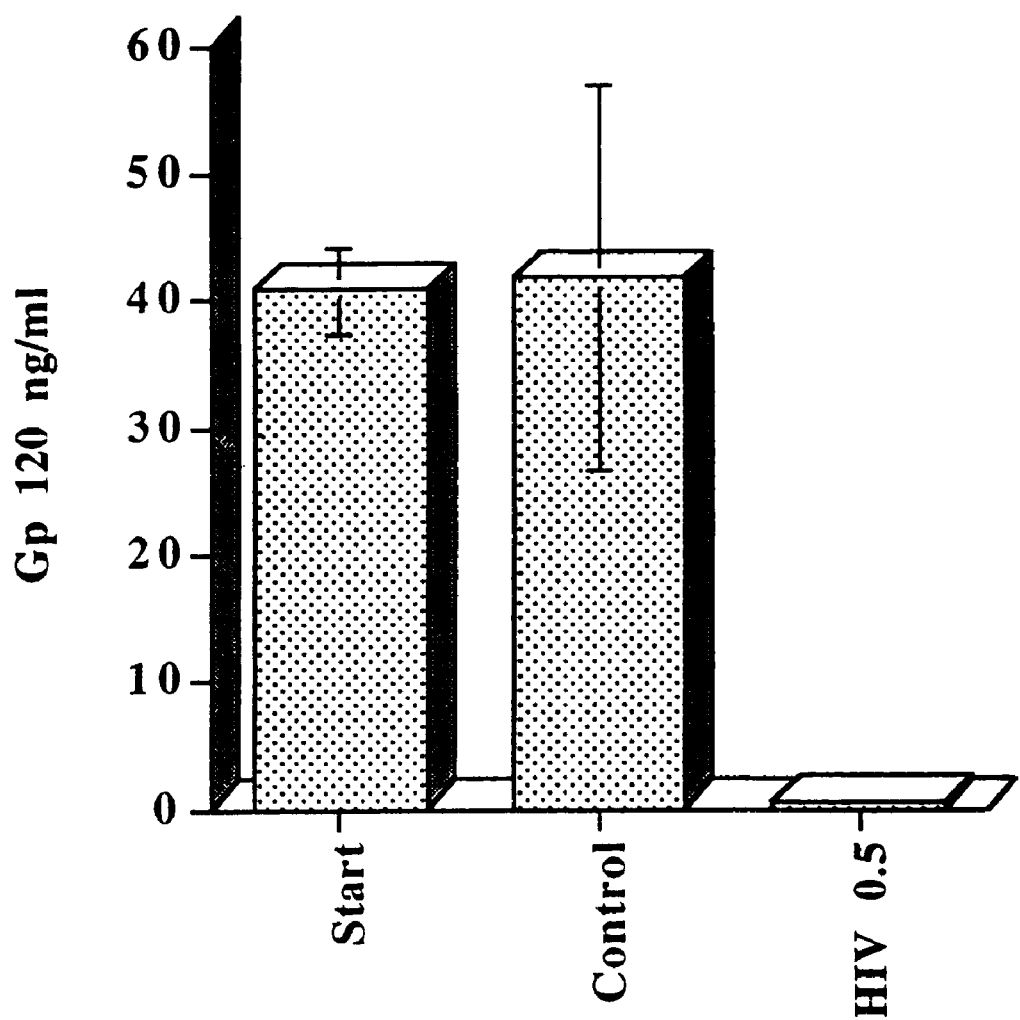
FIG. 4 is a graphic representation of the removal of gp120 from culture media by an anti-HIV column according to the method of the present invention.

The term "target molecules" as used herein for the purposes of specification and claims, means, a molecule which exhibits binding specificity to an affinity molecule. The target molecule may be the whole molecule as it occurs in the intact virus or may be a part thereof.

The term "affinity molecule" as used herein for the purposes of specification and claims, means, a molecule having specific affinity for the target molecule. Thus, an antibody (monoclonal or polyclonal) that specifically binds to a molecule or ligand of interest, or an oligonucleotide sequence that hybridizes to a nucleic acid of interest such as the viral RNA, are examples of affinity molecules. The ligand that the antibody binds to, and the nucleic acid sequence that the oligonucleotide probe hybridizes to, are the target molecules.

The term "viral load" as used herein for the purpose of specification and claims, refers to all forms of virus or fragments or components thereof in a fluid such as blood, especially all forms of HIV or fragments thereof. Thus, it includes intact virions, fragments thereof, and free viral nucleic acid.

Since the identification of HIV as the causative agent for AIDS, methods for the ex-vivo killing of HIV have been established. Screening of blood products and donors for the presence of HIV has become routine (Fauci et al., 1998, supra). Sensitive PCR and hybridization techniques have been developed to quantify HIV in blood samples (Urdea et al., 1993, AIDS 7 Suppl 2: S11–4; Wilber, 1997, Immunol Invest 26:9–13.). The present invention provides a method for reducing the viral load by extracorporeal treatment of the individual's blood. The method comprises the steps of obtaining a patient's blood, contacting the blood with immobilized affinity molecules specific for the virus, and returning the unbound blood to the individual. The affinity molecules of the present invention may be directed to the viral nucleic acid or to viral proteins. In a preferred embodiment, the method of the present invention is carried out by using an affinity cartridge. The method of the present invention can be carried out by using the device illustrated in FIG. 1. Devices of this general type are disclosed in U.S. Pat. Nos. 4,714,556 and 4,787,974, the disclosures of which are incorporated herein by reference. In this device, blood is passed through the lumen of a hollow fiber ultrafiltration membrane which is in intimate contact, on the non-blood wetted side of the membrane, with immobilized affinity molecules which form means to accept and immobilize viruses. Thus, the ultrafiltration membrane will retain the intact virions and free viral nucleic acid while allowing other components to pass through the lumen. HIV is the prototypic virus for which this invention is described, but the invention can be adapted to the removal of any blood-borne viruses. The device, described in detail in U.S. Pat. Nos. 4,714,556 and 4,787,974, includes multiple channels of hollow-fiber ultrafiltration membrane which form a filtration chamber. An inlet port and an effluent port are in communication with the filtration chamber.

The ultrafiltration membrane is preferably an anisotropic membrane with the tight or retention side facing the bloodstream. The membrane is conveniently formed of any number of polymers known to the art. For example, polysulfone, polyethersulfone, polyamides, polyimides, cellulose acetate, and polyacrylamide. Preferably, the membrane has pores 200–500 nm in diameter, which will allow passage of intact viruses and viral particles and fragments (i.e., HIV virion 110 nm diameter), but not most blood cells (red blood cells 2,000 nm diameter, lymphocytes 7,000–12,000 nm diameter, macrophages 10,000–18,000 nm diameter). A diagram of the device is shown in FIG. 1. A cross-section of the device is shown in FIG. 2. A cross-section of an individual hollow-fiber membrane is shown in FIG. 3. Referring to FIG. 1, chamber 12 contains a plurality of hollow-fiber membranes. These membranes preferably have a 0.3 mm inside diameter and 0.5 mm outside diameter.

For the method of the present invention, blood is withdrawn from a patient and contacted with the ultrafiltration membrane having target molecules. In a preferred embodiment, the blood is separated into its plasma and cellular components. The plasma is then contacted with the affinity molecules specific for the virus, to remove the virus or components thereof. Following removal of virions and/or free nucleic acid, the plasma can then be recombined with the cellular components and returned to the patient. Alternatively, the cellular components may be returned to the patient separately. The treatment can be repeated periodically until a desired response has been achieved. For example, the treatment can be carried out for 2 hours every two weeks. Thus, the essential steps of the present invention are (a) contacting the body fluid with the affinity molecule immobilized to an ultrafiltration membrane under conditions that allow the formation of bound complexes of the affinity molecules and their respective target molecules; (b) collecting unbound materials; and (c) reinfusing the unbound materials into the patient.

The affinity molecules of the present invention may be directed toward proteins/peptides or nucleic acid sequences of the virions. The affinity molecules for the nucleic acid sequences are generally oligonucleotide sequences that are complementary to the viral sequence. The viral nucleic acids become accessible to affinity molecules partly because free viral RNA may be released from dying cells, or cells that contain defective viruses (as may occur during anti-viral therapy). It is preferable to use affinity molecules directed toward nucleic acid sequences or epitopes that are conserved in the virus. For example, for HIV-1, some of the conserved regions include 5' and 3' LTR and regions of the env gene. In a preferred embodiment, probes are designed for the 5' LTR region. When the target molecule is a protein, the epitopes may be selected from conserved regions of the viral coat proteins that are accessible to antibodies in the intact virus. Such regions include, but are not limited to, V3 loop of gp120.

The technology to immobilize enzymes, chelators, and antibodies in dialysis-like cartridges has been developed (Kalghatgi et al., 1980, *Res. Commun. Chem. Pathol. Pharmacol.*, 27:551–61; Ambrus, 1978, *Science*, 201:837–839) and is incorporated herein by reference. These cartridges can be directly perfused with blood from patients through direct venous access, and returned to the patients without further manipulations. Alternatively, blood can be separated into plasma and cellular components by standard techniques. The cellular components may be combined with the plasma before reinfusing or the cellular components can be reinfused separately. Viral load can be assessed in the effluent from the cartridge by standard techniques such as ELISA and nucleic acid amplification and detection techniques. Prototypic cartridges have been used to metabolize excess phenylalanine (Kalghatgi et al., 1980, supra; Ambrus, 1978, supra) or to remove excess aluminum from patients' blood (Anthone et al., 1995, *J. Am. Soc. Nephrol.*, 6:1271–1277). This technology can be utilized with antibodies or other absorptive materials. An illustration of preparing antibodies for immobilization to the hollow fibers for the method of the present invention is presented in U.S. Pat. Nos. 4,714,556 and 4,787,974.

The technology to immobilize DNA fragments to plastic, which retain the ability to hybridize specifically to HIV, HBV, or HCV, has been developed for in vitro ELISA-like assays (Urdea et al., 1993, supra; Wilber, 1997, supra; Chen et al., 1995, *J. Virol. Methods*, 53:131–137; Deeks et al., 1997, *J. Infect. Dis.*, 176:514–517; Flood et al., 1997, *J. Infect. Dis.*, 176:348–352; Lu et al., 1998, *J. Clin. Lab. Anal.*, 12:121–125; Sherman et al., 1993, *J. Clin. Microbiol.* 31:2679–82), incorporated herein by reference. This same technology can be utilized to immobilize fragments of DNA to dialysis-like cartridges.

For binding of affinity molecules to ultrafiltration membrane, the polymers of the ultrafiltration membrane are first activated, i.e., made susceptible for combining chemically with proteins, by using processes known in the art. Any number of different polymers can be used. To obtain a reactive polyacrylic acid polymer, for example, carbodiimides can be used (Valuev et al., 1998, *Biomaterials*, 19:41–3.). Once the polymer has been activated, the affinity molecules can be attached directly or via a linker. Suitable linkers include, but are not limited to, avidin, strepavidin, biotin, protein A, and protein G. For example, antibodies to viral coat proteins may be bound to strepavidin coated polymers of the ultrafiltration membrane. The strepavidin coated ultrafiltration membrane can also be used for the attachment of oligonucleotide to which a biotin labeled base has been added to the 3' end.

The antibodies may also be directly bound to the polymer of the ultrafiltration membrane using coupling agents such as bifunctional reagents, or may be indirectly bound. For example, Protein A or Protein G may be used to immobilize IgG against specific HIV epitopes.

In a preferred embodiment, Protein G sepharose was used to bind the anti-HIV antibodies, and then crosslinked to the antibodies using a bifunctional reagent.

EXAMPLE 1

This embodiment illustrates a device for the method of the present invention. As shown in FIG. 1, the device comprises a cartridge 10 comprising a blood-processing chamber 12 formed of interior glass wall 14. Around chamber 12 is an optional exterior chamber 16. A temperature controlling fluid can be circulated into chamber 16 through port 18 and out of port 20. The device includes an inlet port 32 for the blood and an outlet port 34 for the effluent. The device also provides one or more ports 48 and 50, for accessing the extrachannel space in the cartridge. As shown in FIGS. 1 and 2, chamber 12 contains a plurality of ultrafiltration membranes 22. FIG. 3 is a cross sectional representation of a channel 22 and shows the anisotropic nature of the membrane. As shown in FIG. 3, a hollow fiber membrane structure 40 is composed of a single polymeric material which is formed into a tubular section comprising a relatively tight ultrafiltration membrane 42 and relatively porous exterior portion 44 in which may be immobilized affinity molecules 46.

During the operation of the device, a solution containing the affinity molecules i.e., the antibody or the oligonucleotide probe is loaded on to the device through port 48, The affinity molecules are allowed to immobilize to the exterior 22 of the membrane in FIG. 2. Unbound affinity molecules can be collected from port 50 by washing with saline or other solutions.

EXAMPLE 2

The preparation of antibodies for immobilization to ultrafiltration membranes is disclosed in U.S. Pat. No. 4,787,984. Activation of polymers is carried out as described in U.S. Pat. No. 4,787,974. An illustration of the method for preparation of affinity molecules for immobilization on the exterior surfaces of the ultrafiltration membranes 22 is as follows.

Antibodies to viral coat proteins (i.e., gp 120 of HIV), and a linker (such as strepavidin), which are known in the art, are dissolved at concentrations of 50–200 mg/ml each, in phosphate-buffered saline pH 7.0. Glutaraldehyde in a concentration of 0.1% is added to the antibody and strepavidin solution and incubated for 12 hours at 4° C. Excess glutaraldehyde is removed by adding glycine to the solution at the end of the reaction. The solution is then dialyzed with normal saline using a membrane that excludes molecules larger than 50,000 Daltons, and allowed to react with an activated polymer resulting in a polymer having the antibody and strepavidin irreversibly crosslinked to it. oligonucleotides that will hybridize to the viral genome of interest (i.e., HIV) are synthesized with the addition of a biotin-labeled base at the 3' end. Appropriate sequences for oligonucleotide synthesis are known in the art. The biotin-labeled oligonucleotides are allowed to react with the strepavidin-coupled polymers, resulting in hollow-fiber membranes which have both antibodies and oligonucleotides irreversibly bound.

The cartridges consisting of hollow-fiber membranes with coupled antibodies and oligonucleotides are washed with one liter of sterile saline and then sterilized by exposure to 7% ethylene oxide in carbon dioxide. The cartridges can then be perfused with the blood or plasma of a patient, containing the designated viral infection, through direct venous-venous or venous-arterial access, similar to home-dialysis cartridges. This technology is well established (Pastan et al., 1998, *N. Engl. J. Med.* 338:1428–1437) and this disclosure is incorporated herein by reference. In one embodiment, the virus can be activated by interleukin-2 or the like, prior to the filtration procedure. Activation of the virus releases viral components into the blood circulation of the patient.

EXAMPLE 3

This embodiment illustrates that oligonucleotides directed toward specific regions of the HIV-1 virus can be used for reducing the viral load of HIV-1 in plasma of blood. Suitable regions for construction of oligonucleotide probes can be identified by comparing known sequences of various HIV-1 strains. As those skilled in the art will recognize, many software tools are available for comparison of sequences for identifying conserved regions. For example, an HIV-1 probe, as shown in SEQ ID NO:1, was identified using a commercially available software (BLAST) and is the complement of a conserved sequence in the 5' LTR region. This sequence has been found to be conserved in many different HIV-1 strains.

In another illustration of this embodiment, a conserved sequence from the 5' NTR region for the HCV virus was also identified. A probe complementary to this conserved sequence is disclosed as SEQ ID NO:2.

EXAMPLE 4

This embodiment demonstrates that various antibodies can be identified that recognize surface antigens in viruses. Antibodies to the exposed regions of HIV and HCV can be generated by methods that are well known in the art. Further, antibodies to HIV proteins can also be obtained through the NIH AIDS Research and Reference Reagent Program. For example, monoclonal antibody 902 (catalog no. 522) to gp120 is dislcosed as reacting with the immunodominant hypervariable loop of gp120 of HIV-LLAV and HTLV-IIIB strains of HIV. A monoclonal antibody F 105 (catalog no. 857) binds to gp120 of the surface of IIIB, SF2, MN, RF, and CC-infected cells. Two other monoclonal antibody, 257-D and 268-D (catalog nos. 1510 and 1511) bind to HIV-1MN V3 epitope KRIHI, and HIGPGR respectively. Both antibodies are reported to neutralize HIV-1MN infection of MT-2 cells. A monoclonal antibody, ID6, (catalog no. 2342) reacts with gp120 in IIB and RF assays. In a preferred embodiment, antibodies specific for a plurality of epitopes are bound to the cartridge. In another illustration of this embodiment, antibodies to surface proteins of HCV can be used. The methodologies for identifying and generating antibodies to surface exposed epitopes are known to those skilled in the art. Some antibodies are also available commercially, such as Catalog no. MA5-692p from Harlan Bioproducts, no. 434–26 from Signet laboratories, no. 141925-11 from U.S. Biological, and no.2235-11 from Innogenex.

EXAMPLE 5

This embodiment demonstrates that the method of the present invention can reduce the viral load in a fluid when it is circulated through the hollow fiber to which are immobilized affinity molecules. In one illustration of this embodiment, an anti-HIV DNA-sepharose was prepared from avidin sepharose (Pierce Chemical Co.). Five ml of avidin sepharose was washed three times with binding buffer (20 mM sodium phosphate, 500 mM NaCl, pH 7.5). The oligonucleotide probe of SEQ ID NO:1 was used as the anti-HIV DNA probe. The probe was labeled with biotin and the product purified by using a commercially available biotin labeling kit (GIBCO/BRL) as follows. A total of 2.7 mg anti-HIV DNA probe of SEQ ID NO:1 was dissolved in 1 ml water and added to 5 ml avidin sepharose in 10 ml binding buffer. The reagents were gently shaken at 4° C. overnight and the sepharose was washed three times in phosphate buffered saline (PBS). A total of 5 ml sepharose was suspended in 10 ml PBS and stored at 4° C.

The anti-gp120 sepharose was prepared by combining antibodies to gp 120 from several sources: NIH AIDS Reference Reagents #902 (30 ug), #F105 (199 ug), #489.1 (110 ug), HIV 1 V3 (0.5 ml), 4.8D (200 ug), AD3 (1 ml), ID6 (1 ml), IgG1 b12 (100 ug), and INTRACEL corporation (Issaquah, Wash.) rabbit anti-gp 120 (catalog #00401; 1 ml serum). The ImmunoPure Protein G Plus Orientation kit (catalog #44990zz) was purchased from Pierce Chemical company. The antibodies utilized were in the form of sera of lyophilized antibodies, which were reconstituted as directed, with water. The antibodies were all pooled and diluted 1:1 with binding buffer (50 mM sodium borate, pH 8.2). Two ml protein G sepharose was washed 3 times with 5 ml binding buffer. The antibody solution was then added to the protein G sepharose and gently shaken at room temperature for 30 minutes. The sepharose was then washed three times with 5 ml binding buffer. Thirteen mg DSS (Disuccinumidyl subeterate) was dissloved in 1 ml DMSO and 1.5 ml cross linking buffer (0.15M NaCl, 0.1M Na2PO4, pH 7.2). The DSS solution was added to the protein G sepharose containing the anti-gp120 antibodies and gently shaken at room temperature for 1 hour. The gel was washed with 5 ml cross-linking buffer. After washing, 2 ml of blocking buffer (0.1M ethanolamine, pH 8.2) was added and the sepharose gently shaken at room temperature for 10 minutes. The sepharose was washed twice with 5 ml elution buffer (primary amine containing buffer, pH 2.8), three times with 5 ml binding buffer, and three times with 5 ml PBS. The sepharose was stored at 4° C. in 5 ml PBS. Anti-HIV columns can be prepared by loading the anti-gp120 sepharose or anti-HIV DNA sepharose or both.

To illustrate the use of the above sepharose for removing virus or fragments or components thereof, an anti-HIV column was prepared by using a Microkros filtration device (0.5 um pore size; Spectrum, Laguna Hills, Calif.). No leakage of sepharose was observed with these cartridges. The cartridge was loaded with of anti-gp120 and anti-HIV DNA sepharose, prepared as described above. For this experiment equal amounts of anti-gp120 and anti-HIV DNA sepharose were used. The control cartridge contained albumin sepharose. For each experiment, 4 ml of medium was passed back and forth through the cartridge about 20 times over a period of 30 minutes to provide adequate time for the viral particles or fragments or components thereof in the supernatants to cross the membranes and bind the sepharoses. The effluent was assayed for the presence of gp120 by a commercially available ELISA kit (INTRACEL corp.).

To demonstrate that the anti-HIV column effectively removed the viral proteins, gp120 was mixed with 4.0 ml of RPMI medium containing 10% fetal calf serum and passed through the column. The effluent was assayed for gp120. As shown in FIG. 4, the effluent through the anti-HIV column reduced the amount of gp120 while control column had no effect.

Figure 5A:
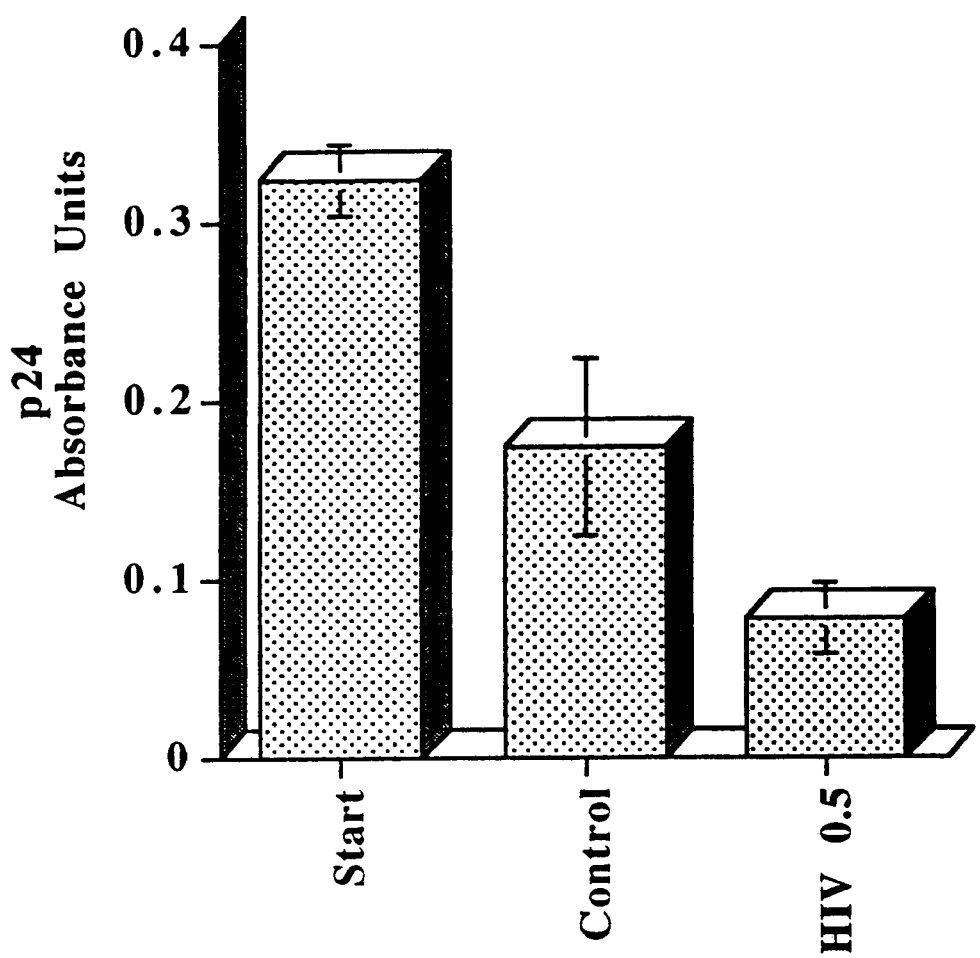
FIGS. 5a and 5b are graphic representations of removal of HIV from the supernatant of HL 2/3 cells using anti-HIV column.
Figure 5B:
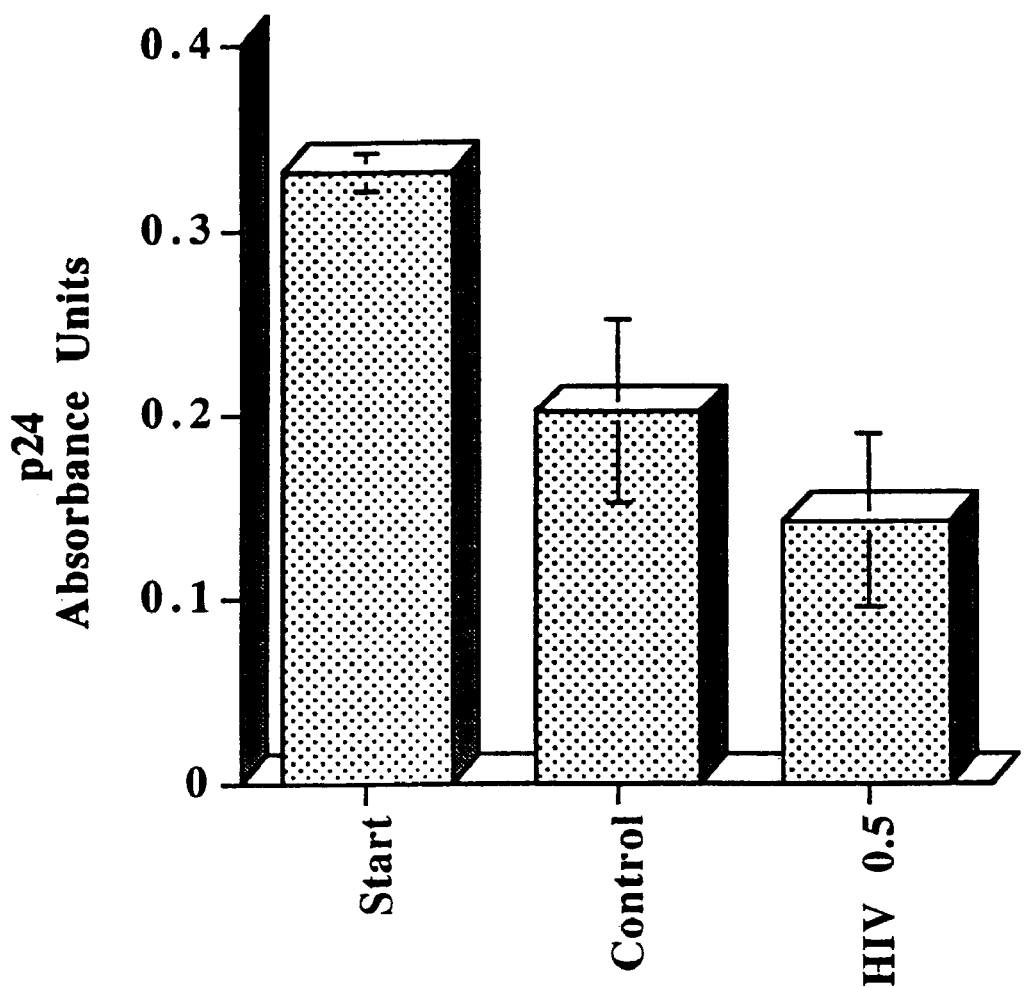

To demonstrate that the anti-HIV column retains HIV particles, supernatant from the cell line HL 2/3 was used. HL 2/3 is a cell line which makes a reverse transcriptase defective virus and various viral particles and RNA (1995, AIDS Res. Hum. Retroviruss 6(11):1281–1285). FIGS. 5$a$ and 5$b$ show the results of two different experiments. In both experiments p24 absorbance was carried out to estimate HIV particles. As shown in FIGS. 5$a$ and 5$b$, anti-HIV columns reduced the HIV particles to a greater extent, than the control columns.

From the foregoing, it will be obvious to those skilled in the art the various modifications in the above-described methods, and compositions can be made without departing from the spirit and scope of the invention. Accordingly, the invention may be embodied in other specific forms without departing from the spirit or essential characteristics thereof. Present examples and embodiments, therefore, are to be considered in all respects as illustrative and not restrictive, and all changes which come within the meaning and range of equivalency of the claims are therefore intended to be embraced therein.

We claim:

1. A method of reducing virions and free viral nucleic acids in the blood of an individual infected with a virus, comprising the steps of:
   a) obtaining blood from the infected individual;
   b) passing the blood through a hollow fiber membrane, wherein affinity molecules are immobilized within a porous exterior portion of the membrane, said affinity molecules comprising molecules having specific affinity for viral nucleic acids and molecules having specific affinity for surface exposed epitopes of viral coat proteins;
   c) collecting the unbound blood; and
   d) reinfusing the unbound blood into the individual.

2. The method of claim 1, wherein the affinity molecule having specific affinity for viral nucleic acids is a nucleic acid sequence.

3. The method of claim 2, wherein the nucleic acid sequence is SEQ ID NO:1.

4. The method of claim 2, wherein the nucleic acid sequence is SEQ ID NO:2.

5. The method of claim 1, wherein the affinity molecule having specific affinity for surface exposed epitopes of viral coat proteins is an antibody directed to loop V3 of gp120 protein.

6. The method of claim 1, wherein the virus is HIV-1.

7. The method of claim 1, wherein the virus is HCV.

8. The method of claim 3, wherein the affinity molecule further comprises an antibody directed to loop V3 of gp120 protein.

9. The method of claim 1, wherein the affinity molecules are attached to a solid matrix prior to being immobilized within the porous exterior surface of the membrane.

10. The method of claim 9, wherein the solid matrix is sepharose.

11. A method of reducing virions and free viral nucleic acids in the plasma of an individual infected with a virus, comprising the steps of:
   a) obtaining blood from the infected individual;
   b) separating the blood into plasma and cellular components;
   c) passing the plasma through a hollow fiber membrane, wherein affinity molecules are immobilized within a porous exterior portion of the membrane, said affinity molecules comprising molecules having specific affinity for viral nucleic acids and molecules having specific affinity for surface exposed epitopes of viral coat proteins;
   d) collecting the unbound plasma; and
   e) reinfusing the cellular components and unbound plasma into the individual.

12. The method of claim 11, wherein the unbound plasma is combined with the cellular components before reinfusing into the individual.

13. The method of claim 11, wherein the affinity molecule having specific affinity for viral nucleic acids is a nucleic acid sequence.

14. The method of claim 13, wherein the nucleic acid sequence has the sequence of SEQ ID NO:1.

15. The method of claim 13, wherein the nucleic acid sequence has the sequence of SEQ ID NO:2.

16. The method of claim 11, wherein the virus is HIV-1.

17. The method of claim 11, wherein the virus is HCV.

18. The method of claim 11, wherein the affinity molecule having specific affinity for surface exposed epitopes of viral coat proteins is an antibody directed to loop V3 of gp120 protein.

19. The method of claim 14, wherein the affinity molecules further comprise an antibody directed to loop V3 of gp120 protein.

20. The method of claim 11, wherein the affinity molecules are attached to a solid matrix prior to being immobilized within the porous exterior portion of the membrane.

21. The method of claim 20, wherein the solid matrix is sepharose.

* * * * *